United States Patent [19]

Bessell

[11] Patent Number: 5,126,377
[45] Date of Patent: Jun. 30, 1992

[54] CATALYST FOR CONVERSION OF SYNTHESIS GAS INTO HYDROCARBONS

[75] Inventor: Sandra Bessell, Victoria, Australia

[73] Assignee: The Broken Hill Proprietary Company Limited, Melbourne, Australia

[21] Appl. No.: 579,637

[22] Filed: Sep. 10, 1990

[30] Foreign Application Priority Data

Sep. 11, 1989 [AU] Australia ............... PJ 6288

[51] Int. Cl.$^5$ ............................................. C07C 1/04
[52] U.S. Cl. ................................................. 518/714
[58] Field of Search ..................................... 518/714

[56] References Cited

U.S. PATENT DOCUMENTS

| | | | |
|---|---|---|---|
| 4,086,262 | 4/1978 | Chang et al. | 260/449.6 |
| 4,628,133 | 12/1986 | Miderhoud et al. | 518/714 |
| 4,632,941 | 12/1986 | Coughlin | 518/714 |
| 4,640,766 | 2/1987 | Post et al. | 518/714 |
| 4,659,743 | 4/1987 | Rao et al. | 518/715 |

FOREIGN PATENT DOCUMENTS 040444 11/1981 European Pat. Off. .
050911 5/1982 European Pat. Off. .
211228 2/1987 European Pat. Off. .

*Primary Examiner*—Howard T. Mars
*Attorney, Agent, or Firm*—Nikaido, Marmelstein, Murray & Oram

[57] ABSTRACT

Processes for converting synthesis gas into hydrocarbons by passing the synthesis gas over a catalyst, and catalysts suitable for use in such processes. The catalysts include cobalt supported on ZSM-5 type zeolites and they also include chromium.

12 Claims, No Drawings

CATALYST FOR CONVERSION OF SYNTHESIS GAS INTO HYDROCARBONS

BACKGROUND

The invention relates to catalyst compositions for use in the Fischer-Tropsch process for the conversion of synthesis gas into hydrocarbons, and an improved process using these catalyst compositions. It is particularly aimed at producing hydrocarbons suitable for use as liquid fuels.

The Fischer-Tropsch process is well known and described in various texts such as "The Fischer-Tropsch and Related Synthesis" by H. H. Storch, N. Golumbic and R. B. Anderson (John Wiley and Sons, New York, 1951). Generally this process takes place over metals such as iron, cobalt, nickel and ruthenium, which may be supported on carriers such as kieselguhr or silica. While nickel preferentially produces methane from synthesis gas, iron, cobalt and ruthenium produce a broad weight range of hydrocarbons ranging from methane to heavy waxes and consist principally of linear paraffins and olefins.

The hydrocarbons distributions of these products generally follow the Schulz-Flory distributions, which may be represented by the following equation:

$$W_n + n\alpha^{n-1}(1-\alpha)^2$$

where W is the weight fraction of the product with a carbon number n, and $\alpha$ (commonly known as the alpha value) is the probability of chain growth, and is assumed to be independent of chain length.

There is some deviation from this equation, especially at lower carbon numbers where independence of chain growth is less likely. Methane makes are generally "higher than expected", and other low carbon fractions are generally "lower than expected". This is believed to be caused by methane being formed by additional mechanisms such as cracking, and greater reactivity of lower olefins. (especially ethylene) towards chain growth.

As the products are predominantly straight chained in nature, the octane number of the gasoline fraction of the resulting liquid product is low. Thus in order to produce hydrocarbons suitable for use as liquid fuels, it is desirable to limit the chain length of the product to essentially the diesel range, and to produce a gasoline fraction of enhanced octane number by increasing levels of branching and/or aromatics in the product.

Zeolites are crystalline aluminosilicates with shape selective and acidic properties, and are further described in texts such as "Zeolite Molecular Sieves" by D. W. Breck (John Wiley and Sons, New York, 1974). They, and ZSM-5 in particular, have been found to be extremely effective in converting methanol into highly aromatic gasoline range hydrocarbon mixtures.

Two different approaches using zeolites as catalyst components have been tried in order to achieve the abovementioned desirable results.

The first approach consists of using a catalyst mixture comprising a methanol synthesis catalyst and a zeolite.

For example, AU 53272/79 (Shell International Research Maatschappi BV) describes the use of a mixture of two catalysts to produce an aromatic hydrocarbon mixture. The first of these catalysts is capable of converting a $H_2/CO$ mixture into acrylic oxygen contained hydrocarbons, whilst the second is a crystalline silicate. A catalyst containing zinc together with chromium was said to be very suitable for use as the first catalyst.

However, results obtained using this approach have proved to be disappointing, as in order to obtain reasonable conversion, too much methane is formed. This is due to the considerably different favorable temperature, pressure regimes for the operation of the two different catalysts.

The second approach uses bi-functional catalyst systems in which an active Fischer-Tropsch metal component is mixed and/or incorporated into or onto a zeolite, e.g.:

(i) U.S. Pat. No. 4,086,262 (Mobil Oil Corporation) describes the use of zeolites such as ZSM-5 as supports for Fischer-Tropsch metals including iron, cobalt, nickel, ruthenium, thorium, rhodium and osmium, to produce hydrocarbons from synthesis gas.

(ii) AU 34883/84 (Union Carbide Corp.) describes the use of catalyst compositions consisting of steam-stabilized Zeolite Y as a catalyst support for conventional Fischer-Tropsch metals such as iron or cobalt. These compositions enhanced branching and aromatization in the products, as well as the amount of product boiling in the liquid fuel range.

(iii) AU 88929/82 (U.S. Department of Energy) describes a catalyst composition of cobalt, promoted with thoria, on a ZSM-5 type zeolite support to produce high octane liquid hydrocarbon products that are in the gasoline boiling range, but contain branched aliphatic hydrocarbons rather than aromatics to impart high octane numbers.

The specifications of Australian Patent Nos. 559306, 562460, 566159, 567204 and 570126 disclose Fischer-Tropsch catalysts comprising cobalt and a promoter supported on silica and/or alumina. In each specification chromium is mentioned as a suitable promoter. The catalysts exemplified in these specifications have relatively high cobalt loadings. Furthermore there is no indication that incorporation of chromium into the catalyst system decreases methane selectivity and increases liquid hydrocarbon selectivity.

While cobalt catalysts have higher activities and selectivities to liquid range hydrocarbons, iron catalysts are currently preferred because of the excessive amounts of methane produced by cobalt catalysts. Cobalt catalysts can produce ten times the amount of methane predicted by the Schulz-Flory equation, whilst excess methane produced by iron catalysts is generally minimal.

Thus there is considerable incentive to reduce the amount of methane produced by cobalt Fischer-Tropsch catalysts in order to make these catalysts commercially viable. It is therefore an object of the invention to reduce methane selectivity and increase liquid range hydrocarbon selectively for cobalt Fischer-Tropsch catalysts, whilst maintaining high catalyst activity, and producing a high octane gasoline fraction.

SUMMARY OF THE INVENTION

It has now been found that addition of chromium to catalyst compositions containing cobalt, promoted or unpromoted, supported on ZSM-5 type zeolites produces a catalyst of increased Fischer-Tropsch activity, which gives reduced methane and increased liquid range hydrocarbon selectivities, whilst maintaining high levels of branching (and hence a high octane number) in the gasoline fraction. The invention accordingly provides a catalyst for the conversion of synthesis gas into hydrocarbons, comprising cobalt supported on a ZSM-5 type zeolite, characterized in that the catalyst also contains chromium. The invention also provides a process for the conversion of synthesis gas into hydrocarbons using a catalyst comprising cobalt supported on a ZSM-5 type zeolite, characterized in that the catalyst also contains chromium.

DETAILED DESCRIPTION OF THE INVENTION

The synthesis gas for conversion comprises substantial proportions of carbon monoxide and hydrogen and may also contain smaller amounts of carbon dioxide, water, methane and nitrogen. It may be obtained from carbonaceous sources such as coal, oil shale, petroleum hydrocarbons and natural gas by known processes such as partial oxidation, gasification and steam reforming.

The relative concentrations of the gaseous components depend on the source of the synthesis gas and the process by which it is obtained. Coal derived synthesis gas is characterized by relatively low hydrogen to carbon monoxide ratios (typically of the order of 0.5 mole/mole), whilst natural gas derived synthesis gas is characterized by relatively high hydrogen to carbon monoxide ratios (typically of the order of 2 or greater).

We have been particularly interested in natural gas derived synthesis gas as a means of utilizing Australia's abundant natural gas reserves, however, the process of the invention is not limited to the high hydrogen content synthesis gas derived from natural gas. Desirable hydrogen to carbon monoxide molar ratios of the synthesis gas for conversion would be in the range of 0.2 to 6.

The invention is concerned with the lowering of methane selectivity and increasing the liquid range hydrocarbon selectivity of cobalt Fischer-Tropsch catalysts, whilst maintaining high catalyst activity, and producing a high octane gasoline fraction. Thus cobalt is an essential part of the catalyst composition, and may be present in an amount of 1 to 50 weight percent based on the total weight of the catalyst composition. Preferably cobalt comprises from 5 to 10 percent by weight of the total weight of the catalyst.

In order to produce a high octane number gasoline fraction it is necessary to use an acidic support in the catalyst composition. Zeolites of reasonably high silica to alumina ratios, i.e. 10 or higher, fulfill this requirement. These zeolites are exemplified by the ZSM-5 type zeolites which include ZSM-5, ZSM-11, ZSM-12, ZSM-35, ZSM-38 and other similar materials. Particularly favored are the small crystal variations of these ZSM-5 type zeolites, as described in our co-pending Australian patent application No. 44747/89, (corresponding to U.S. patent application Ser. No. 439,973 in which ZSM-5 type zeolites of 5$\mu$m or less, or more preferably 1 $\mu$m or less, are used as supports to produce a highly branched, and hence high octane, liquid hydrocarbon product. The ZSM-5 type zeolite should be present in the formulation in an amount of from 10 to 98 weight percent.

It is known to those skilled in the art that thoria and other basic oxides can be used as promoter material for cobalt Fischer-Tropsch catalysts in order to improve catalyst activity and selectivity. As we have found chromium addition to be beneficial to both these promoted and unpromoted catalysts, the presence of these promoter materials is optional, but preferred. Thoria or other basic oxide promoters may be present in an amount of from 0.01 to 25 weight percent.

Chromium is used as an additive to the above described catalyst formulation to achieve the desired reduced methane selectivity and increase liquid range hydrocarbon selectivity, whilst increasing catalyst activity. For the purposes of the invention chromium is preferably present in an amount of from 0.01 to 25 weight percent based on the total weight of the catalyst composition, more preferably between 0.05 and 5 weight percent.

The cobalt, promoter and chromium may be loaded onto the ZSM-5 type zeolite support by any of the methods known to those skilled in the art. These methods include:

(i) mixture of the appropriate oxides and zeolite support.

(ii) precipitation of the metals from solution as carbonates, followed by drying, calcining and mixing the resulting oxides with the zeolite support.

(iii) precipitation of the metals as carbonates on the zeolite support, followed by drying and calcination.

(iv) impregnation of the zeolite support with appropriate metal carbonyl solutions and/or appropriate soluble metal salt solutions, followed by drying and calcination. Aqueous or organic solutions may be used as appropriate.

Before use in synthesis gas conversion, the catalyst of the invention is reduced or activated. As is known by those skilled in the art, hydrogen, synthesis gas or another reductant may be used for this reduction step under conditions of elevated temperature and pressures of atmospheric to the pressures used in the synthesis. Typical reduction temperatures are of the order of 250° C.–350° C., with pressures of from atmospheric to 3.5 MPa typically being used.

The Fischer-Tropsch process can be performed over a wide range of temperatures, pressures and space velocities. However, there are some limitations on the temperature range used if the catalyst of this invention is to be effective. In order for the zeolite to be effective in producing branched hydrocarbons the system must be at a temperature at which oligomerization and isomerization reactions can occur on the zeolite. This places a lower limit of 200° C. on the reaction. As the temperature is increased cracking reactions begin to occur, and at high temperatures of 350° C. and above, so much methane is produced that any benefits derived from the addition of the chromium to the catalyst formulation would not be realized. Preferably the reaction temperature is maintained in the range from 220° C. to 280° C. and most preferably in the range from 220° C. to 260° C.

Typical pressures used in the synthesis are of the order of from 0 to 5 MPa, usually from 1 to 3.5 MPa, whilst typical space velocities are at GHSV's of the order of from 10 to 10000 hr$^{-1}$ usually from 50 to 5000 hr$^{-1}$.

The following examples illustrate preferred embodiments of the invention as well as embodiments of the prior art.

EXAMPLE 1

Preparation of Zeolite AGP8

A solution prepared from 75.9 g aluminum wire and 456.0 g sodium hydroxide in 33 l water was added to 20.01 kg Ludox ® (40% silica) and stirred well. 4.434 kg of tetrapropylammonium bromide, 7.5 kg of sodium chloride, as well as an extra 5 l of water, were added with stirring.

The resulting mixture was charged to a 57 l stirred autoclave and crystallized at 170° C. for 12 hours. The resulting product was filtered and washed.

EXAMPLE 2

Preparation of Zeolite R317/2

Three solutions were prepared. The first consisted of 1.54 g of aluminum wire dissolved in a solution of 6.9 g sodium hydroxide in 100 g water, the second of 64.7 g tetrapropylammonium bromide dissolved in 100 g water, and the third of 86.7 g Cab-O-Sil ® mixed in 1200 g water.

These three solutions were stirred together for 15 minutes and 23 g sodium hydroxide was added to form a gel.

The resulting mixture was placed in a 2 l stirred autoclave and maintained at autogeneous pressure at 170° C. for 20 hours. The resulting product was filtered and washed.

EXAMPLE 3

Preparation of Zeolite MA3

A solution of 16.74 kg of Ludox ® (40% silica) in 6 l of water was stirred while adding a solution of 1000 g tetrapropylammonium bromide in 3 l water.

A solution of 225 g sodium aluminate in 600 ml water was added to 900 g sodium hydroxide in 2 l water.

The above two resulting solutions were mixed, well stirred and made up to 45 l with water. The mixture was then charged to an autoclave and maintained at 100° C. for 6 days and 170° C. for two days. The resulting product was filtered and washed.

The zeolites of Examples 1 to 3 were examined by X-ray diffraction and were found to display the typical X-ray diffraction patterns of ZSM-5. Chemical analysis and scanning electron microscopy was also performed on these zeolites, and they were found to have the following characteristics.

| | |
|---|---|
| Example 1(AGP8): | $SiO_2/Al_2O_3$ = 89 (mole/mole); mixture of small (1 μm) and large (10 μm) crystals. |
| Example 2(R317/2): | $SiO_2/Al_2O_3$ = 50 (mole/mole); aggregates of variable sized relatively small (1 μm–5 μm) crystals. |
| Example 3(MA3): | $SiO_2/Al_2O_3$ = 79 (mole/mole); aggregates of small (0.2 μm–0.5 μm) crystals. |

Prior to further use in the catalyst preparations, the zeolites were converted to the hydrogen form. This was done by either subjecting the zeolite to two $NH_4^+$ exchange treatments with 1 M ammonium nitrate solution, followed by calcination at 550° C., or by two acid washes with a 1 M HCl solution.

EXAMPLES 4 TO 22

Preparation of Catalysts

The zeolites of Examples 1 to 3, as well as a commercially obtained Zeolite Y (Linde LZ-Y82) which had been calcined at 500° C., a commercial activated alumina (Alltech Associates), a commercially available silica and a commercially available kieselguhr were impregnated with appropriate amounts of aqueous solutions of cobaltous nitrate, thorium nitrate and chromium nitrate, so as to make the desired catalyst formulation. The silica used was MATREX ™ silica grade 84160 and the kieselguhr used was an acid washed chromatography grade available from Ajax chemicals. The impregnated zeolites were stirred under vacuum for 30 minutes, dried in a microwave oven, and then calcined at 500° C. for approximately four hours. The resulting catalysts identified by their "FT" code names and their desired compositions in parts by weight were as follows:

| | | |
|---|---|---|
| 4. | FT394 | 75 Co:1000 AGP8 |
| 5. | FT395 | 75 Co:5 Cr:1000 AGP8 |
| 6. | FT408 | 75 Co:1000 R317/2 |
| 7. | FT409 | 75 Co:5 Cr:1000 R317/2 |
| 8. | FT381 | 75 Co:1000 MA3 |
| 9. | FT379 | 75 Co:5 Cr:1000 MA3 |
| 10. | FT434 | 75 Co:5 Th:1000 MA3 |
| 11. | FT386 | 75 Co:5 Th:5 Cr:1000 MA3 |
| 12. | FT398 | 75 Co:1000 LZ-Y82 |
| 13. | FT399 | 75 Co:5 Cr:1000 LZ-Y82 |
| 14. | FT404 | 75 Co:1000 Activated Alumina |
| 15. | FT405 | 75 Co:5 Cr:1000 Activated Alumina |
| 16. | FT400 | 75 Co:1000 Kieselguhr |
| 17. | FT401 | 75 Co:5 Cr:1000 Kieselguhr |
| 18. | FT402 | 75 Co:1000 Silica |
| 19. | FT403 | 75 Co:5 Cr:1000 Silica |
| 20. | FT365 | 100 Co:5 Cr:1000 MA3 |
| 21. | FT379 | 75 Co:5 Cr:1000 MA3 |
| 22. | FT370 | 50 Co:5 Cr:1000 MA3 |

The catalysts were then pressed, ground and sieved, and size fractions between 1 mm –2mm were charged to a microreactor for testing. Prior to use, the catalysts were reduced in a stream of hydrogen at atmospheric pressure at 350° C. with a GHSV of 5000 hr$^{-1}$ for 16 hours.

Each catalyst was used to convert a synthesis gas with a 2:1 hydrogen to carbon monoxide molar ratio. Reaction conditions were a temperature of 240° C., a pressure of 2 MPa and a GHSV of 1000 hr$^{-1}$.

The catalysts were run under these conditions for five days, and Table 1 summarizes the average carbon monoxide conversion levels (averages after 30 hours on line) and the product selectivities obtained

TABLE 1

Conversion and Product Selectivities for Various Cobalt Fischer-Tropsch Catalysts With and Without Chromium in Their Formulations
(2:1 $H_2$:CO synthesis gas, 240° C., 2 MPa, GHSV = 1000 hr$^{-1}$)

| Catalyst (Example No.) | Catalyst Composition | % Conversion (Ave. after 30 hours on stream) | Selectivity wt % | | | |
|---|---|---|---|---|---|---|
| | | | $CH_4$ | $CO_2$ | $C_2$-$C_5$ | >$C_5$ |
| 4. | 75 Co:1000 AGP8 | 56 | 29 | 5 | 23 | 43 |
| 5. | 75 Co:5 Cr:1000 AGP8 | 72 | 21 | 4 | 16 | 60 |
| 6. | 75 Co:1000 R317/2 | 62 | 23 | 3 | 16 | 57 |
| 7. | 75 Co:5 Cr:1000 R317/2 | 74 | 22 | 3 | 12 | 63 |
| 8. | 75 Co:1000 MA3 | 45 | 22 | 1 | 20 | 56 |
| 9. | 75 Co:5 Cr:1000 MA3 | 56 | 16 | 1 | 17 | 66 |
| 10. | 75 Co:5 Th:1000 MA3 | 51 | 21 | 2 | 18 | 59 |

TABLE 1-continued

Conversion and Product Selectivities for Various Cobalt Fischer-Tropsch Catalysts With and Without Chromium in Their Formulations
(2:1 $H_2$:CO synthesis gas, 240° C., 2 MPa, GHSV = 1000 $hr^{-1}$)

| Catalyst (Example No.) | Catalyst Composition | % Conversion (Ave. after 30 hours on stream) | Selectivity wt % | | | |
|---|---|---|---|---|---|---|
| | | | $CH_4$ | $CO_2$ | $C_2-C_5$ | $>C_5$ |
| 11. | 75 Co:5 Th:5 Cr:1000 MA3 | 72 | 18 | 2 | 15 | 64 |
| 12. | 75 Co:1000 LZ-Y82 | 19 | 29 | 2 | 28 | 41 |
| 13. | 75 Co:5 Cr:1000 LZ-Y82 | 9 | 30 | 3 | 40 | 27 |
| 14. | 75 Co:1000 Activated Alumina | 46 | 18 | 5 | 18 | 60 |
| 15. | 75 Co:5 Cr:1000 Activated Alumina | 31 | 30 | 7 | 22 | 41 |
| 16. | 75 Co:1000 Kieselguhr | 8 | 2 | 4 | 15 | 80 |
| 17. | 75 Co:5 Cr:1000 Kieselguhr | 42 | 27 | 5 | 18 | 49 |
| 18. | 75 Co:1000 Silica | 35 | 14 | 4 | 18 | 64 |
| 19. | 75 Co:5 Cr:1000 Silica | 42 | 16 | 3 | 16 | 65 |
| 20. | 100 Co:5 Cr:1000 MA3 | 61 | 17 | 2 | 18 | 64 |
| 21. | 75 Co:5 Cr:1000 MA3 | 56 | 16 | 1 | 17 | 66 |
| 22. | 50 Co:5 Cr:1000 MA3 | 38 | 19 | 1 | 30 | 51 |

These results clearly illustrate the invention, with the addition of chromium to all the ZSM-5 supported catalysts improving catalyst activity whilst reducing methane and increasing liquid range hydrocarbon ($>C_5$) selectivity. A similar result is seen on the thoria promoted catalyst, whilst catalysts supported on non-ZSM-5 type supports are not improved by the addition of chromium.

Another object of the invention was to produce a high octane number gasoline fraction. The liquid hydrocarbon products collected at the end of the synthesis gas conversion experiments were analyzed by gas chromatography/mass spectrometry, and proportions of normal paraffins in the individual and total $C_5-C_{18}$ fuel fractions given in Table 2.

products. All the ZMS-5 supported catalysts produced lower n-paraffin content naphthas than the less acidic zeolite Y, silica, kieselguhr and alumina supported catalysts. As the acidity of ZSM-5 was increased, either by increasing alumina content as in R317/2, or by reducing crystal size as in MA3, naphthas with lower proportions of normal paraffins resulted.

Addition of chromium to these catalyst formulations was found to have no significant deleterious effect on production of high octane products, the selection of the support material being much more important. In many cases the addition of chromium had the beneficial effect of decreasing the n-paraffin content of the gasoline fraction whilst increasing the n-paraffin content of the distillate fraction.

TABLE 2

PROPORTIONS OF NORMAL PARAFINS IN THE GASOLINE, AVIATION FUEL AND DISTILLATE FRACTIONS OF THE LIQUID HYDROCARBON PRODUCT FROM VARIOUS COBALT FISCHER-TROPSCH CATALYSTS WITH AND WITHOUT CHROMIUM IN THEIR FORMULATIONS
(2:1 $H_2$:CO synthesis gas, 240° C., 2 MPa, GHSV = 1000 $hr^{-1}$)

| Catalyst (Example No.) | Catalyst Composition | Proportions of Normal Paraffins in Hydrocarbon Product | | | | |
|---|---|---|---|---|---|---|
| | | Light Gasoline $>C_5-C_9$ | Heavy Gasoline $>C_9-C_{11}$ | Aviation Fuel $>C_{11}-C_{13}$ | Distillate $>C_{13}-C_{18}$ | Total $C_5-C_{18}$ |
| 4. | 75 Co:1000 AGP8 | 0.46 | 0.32 | 0.34 | 0.43 | 0.41 |
| 5. | 75 Co:5 Cr:1000 AGP8 | 0.29 | 0.22 | 0.26 | 0.44 | 0.29 |
| 6. | 75 Co:1000 R317/2 | 0.26 | 0.18 | 0.23 | 0.34 | 0.25 |
| 7. | 75 Co:5 Cr:1000 R317/2 | 0.22 | 0.18 | 0.23 | 0.39 | 0.24 |
| 8. | 75 Co:1000 MA3 | 0.18 | 0.14 | 0.14 | 0.30 | 0.18 |
| 9. | 75 Co:5 Cr:1000 MA3 | 0.21 | 0.14 | 0.26 | 0.48 | 0.22 |
| 10. | 75 Co:5 Th:1000 MA3 | 0.20 | 0.15 | 0.20 | 0.45 | 0.20 |
| 11. | 75 Co:5 Th:5 Cr:1000 MA3 | 0.22 | 0.14 | 0.20 | 0.43 | 0.22 |
| 12. | 75 Co:1000 LZ-Y82 | 0.37 | 0.34 | 0.40 | 0.55 | 0.41 |
| 13. | 75 Co:5 Cr:1000 LZ-Y82 | 0.37 | 0.32 | 0.34 | 0.55 | 0.40 |
| 14. | 75 Co:1000 Activated Alumina | 0.72 | 0.77 | 0.82 | 0.88 | 0.80 |
| 15. | 75 Co:5 Cr:1000 Activated Alumina | 0.84 | 0.85 | 0.89 | 0.92 | 0.88 |
| 16. | 75 Co:1000 Kieselguhr | 0.6 | 0.7 | 0.7 | 0.8 | 0.7 |
| 17. | 75 Co:5 Cr:1000 Kieselguhr | 0.8 | 0.9 | 1.0 | 0.6 | 0.8 |
| 18. | 75 Co:1000 Silica | — | 0.85 | 0.89 | — | — |
| 19. | 75 Co:5 Cr:1000 Silica | — | 0.86 | 0.93 | — | — |
| 20. | 100 Co:5 Cr:1000 MA3 | 0.22 | 0.16 | 0.23 | 0.42 | 0.23 |
| 21. | 75 Co:5 Cr:1000 MA3 | 0.21 | 0.14 | 0.26 | 0.48 | 0.22 |
| 22. | 50 Co:5 Cr:1000 MA3 | 0.16 | 0.14 | 0.25 | 0.53 | 0.18 |

The lower the normal paraffin content, the higher the octane number of the resulting fuel, as a drop in the proportion of normal paraffins indicates an increase in the relative proportions of other components, i.e. branched paraffins, normal and branched olefins and aromatics. These other components all have higher octane ratings than normal paraffins, and thus the increase in the overall octane rating of the fuel.

From this table one can see the importance of using a highly acidic support for the production of high octane

EXAMPLES 23 TO 26

The Effect of Temperature on Catalyst Performance

Catalyst used was FT471 which comprised:
75 Cr:5 Th:1000 MA3
Synthesis gas comprising 2:1 $H_2$:CO was converted to liquid hydrocarbons by passing the synthesis gas over the FT471 catalyst at a variety of temperatures whilst maintaining the pressure at 2 MPa and using a GHSV of 1000 hr$^{-1}$.

TABLE 3

| | Temperature °C. | % Conversion | Selectivity (wt %) | | | |
|---|---|---|---|---|---|---|
| | | | CH$_4$ | Co$_2$ | C$_2$-C$_5$ | C$_5$ |
| 23. | 220 | 30 | 18 | 1 | 23 | 58 |
| 24. | 240 | 64 | 16 | 2 | 17 | 65 |
| 25. | 260 | 79 | 26 | 11 | 16 | 47 |
| 26. | 280 | 83 | 34 | 24 | 18 | 24 |

The n-paraffin content of the liquid hydrocarbon products produced under the process conditions of Examples 23 to 26 are set out in Table 4.

TABLE 4

| | Temperature °C. | Proportions n-paraffins | | | | |
|---|---|---|---|---|---|---|
| | | Light gas. | Heavy Gas. | Av. Fuel. | Dist. | Total |
| 23. | 220 | 0.21 | 0.16 | 0.22 | 0.48 | 0.23 |
| 24. | 240 | 0.19 | 0.15 | 0.26 | 0.48 | 0.21 |
| 25. | 260 | 0.18 | 0.13 | 0.17 | 0.25 | 0.17 |
| 26. | 280 | 0.21 | 0.02 | 0.04 | 0.04 | 0.16 |

The above results indicate that at temperatures above 260° C. methane selectivity increases significantly, liquid hydrocarbon selectivity decreases sharply and the n-alkane content of the distillate fraction decreases dramatically.

It will be clearly understood that the invention in its general aspects is not limited to the specific details referred to hereinabove.

The claims defining the invention are as follows, I claim:

1. A process for producing liquid hydrocarbons comprising passing synthesis gas comprising carbon monoxide and hydrogen over a catalyst comprising cobalt and chromium supported on a zeolite of the ZSM-5 family at a temperature in the range from 220° C. to 280° C.

2. A process according to claim 1 wherein the process is performed at a pressure in the range from 1 to 3.5 MPa and a space velocity in the range from 10 to 10,000 hr$^{-1}$.

3. A process according to claim 1 wherein the cobalt comprises from 1% to 50% by weight of the total weight of catalyst.

4. A process according to claim 1 wherein the cobalt comprises from 5% to 10% by weight of the total weight of catalyst.

5. A process according to claim 1 wherein the zeolite is selected from the group consisting of ZSM-5, ZSM-11, ZSM-12, ZSM-35 and ZSM-38.

6. A process according to claim 1 wherein the zeolite comprises crystals having a size no greater than 5 minutes.

7. A process according to claim 6 wherein the crystal size is not greater than 1 micron.

8. A process according to claim 1 wherein the catalyst contains a promoter in an amount from 0.01% to 25% by weight of the total weight of catalyst.

9. A process according to claim 8 wherein the promoter is thoria.

10. A process according to claim 1 wherein the chromium comprises from 0.01% to 25% by weight of the total weight of catalyst.

11. A process according to claim 10 wherein the chromium comprises from 0.05% to 5% by weight of the total weight of catalyst.

12. A process according to claim 1, wherein the synthesis gas is passed over the catalyst at a temperature in the range from 220° C. to 260° C.

* * * * *